US005830677A

United States Patent [19]
Wu et al.

[11] Patent Number: 5,830,677
[45] Date of Patent: Nov. 3, 1998

[54] METHODS AND COMPOSITIONS FOR THE DETECTION OF COLON CANCERS

[75] Inventors: Ying-Jye Wu, Framingham; Susan K. Keesee, Harvard, both of Mass.

[73] Assignee: Matritech, Inc., Newton, Mass.

[21] Appl. No.: 448,048

[22] Filed: May 23, 1995

Related U.S. Application Data

[62] Division of Ser. No. 168,993, Dec. 17, 1993, Pat. No. 5,547,928.
[51] Int. Cl.$^6$ .......................... G01N 33/53; G01N 33/574
[52] U.S. Cl. .......................... 435/7.23; 435/7.21; 436/63; 436/64; 436/813; 530/387.7
[58] Field of Search .................................. 435/7.23, 7.21; 436/63, 64, 813; 530/387.7

[56] References Cited

U.S. PATENT DOCUMENTS

| | | | |
|---|---|---|---|
| 4,775,620 | 10/1988 | Cardiff et al. | 435/7.23 |
| 4,882,268 | 11/1989 | Penman et al. | |
| 4,885,236 | 12/1989 | Penman et al. | |
| 5,158,893 | 10/1992 | Hackett et al. | 435/7.21 |
| 5,273,877 | 12/1993 | Fey et al. | |
| 5,288,614 | 2/1994 | Bodenmuller et al. | 435/7.23 |
| 5,547,928 | 8/1996 | Wu et al. | 514/2 |

FOREIGN PATENT DOCUMENTS

| | | |
|---|---|---|
| 0 337 057 | 1/1989 | European Pat. Off. |
| WO 87/03910 | 7/1987 | WIPO |
| WO92/02558 | 2/1992 | WIPO |
| WO92/05197 | 4/1992 | WIPO |
| WO93/09437 | 5/1993 | WIPO |

OTHER PUBLICATIONS

Anderson et al. (1983) "Provisional Normograms" for Identifying Adenocarcinomas of the Prostate or Colon and Hepatocellular Carcinoma Derived From Their Distribution of Proteins Separated by Two–Dimensional Electrophoresis, *The Prostate* 4: 83–89.

Boffa et al. (1977) "Changes in Chromosomal Proteins in Colon Cancer," *Cancer* 40: 2584–2591.

Keesee et al. (1994) "Nuclear Matrix Proteins in Human Colon Cancer," *Proc. Natl. Acad. Sci. USA* 91:1913–1916.

Tracy et al. (1982) "Patterns for Normal Colon Mucosa and Colon Adenocarcinoma Compared by Two–Dimensional Gel Electrophoresis," *Clin. Chem.* 28: 915–919.

Aebi et al., "The Nuclear Lamina is a Meshwork of Intermediate–Type Filaments", *Nature*, 323:560–564 (1986).

Berezney et al., "Identification of a Nuclear Protein Matrix", *Biochem. Biophys. Res. Commun.*, 60:1410–1417 (1974).

Bidwell et al., "Osteocalcin Gene Promoter–Binding Factors are Tissue–Specific Nuclear Matrix Components", *Proc. Natl. Acad. Sci.*, 90:3162–3166 (1993).

Brancolini and Schneider, "Change in the Expression of a nuclear Matrix–Associated Protein is Correlated with Cellular Transformation", *Proc. Natl. Acad. Sci.*, 88:6936–6940 (1991).

Compton et al., "Primary Structure of NuMA, an Intranuclear Protein that Defines a Novel Pathway for Segregation of Proteins at Mitosis", *J. Cell. Biol.*, 116:1395–1408 (1992).

Dacheng et al., "Core Filaments of the Nuclear Matrix", J. Cell. Biol., 110:569–580 (1990).

Dworetsky et al., "Sequence–Specific DNA–Binding Proteins are Components of a Nuclear Matrix–Attachment Site", *Proc. Natl. Acad. Sci.*, 80:4178–4182 (1992).

Earnshaw and heck, "Localization of Topoisomerase II in Mitotic Chromosomes", *J. Cell. Biol.*, 100:1716–1725 (1985).

Fearon and Vogelstein, "A Genetic Model for Colorectal Tumorigenesis", *Cell*, 61:759–767 (1990).

Fey et al., "Epithelial Cytoskeletal Framework and Nuclear Matrix–Intermediate Filament Scaffold: Thee–dimensional Organization and Protein Composition", *J. Cell Biol.*, 98:1973–1984 (1984).

Fey et al., "The Nonchromatin Substructures of the Nucleus: The Ribonucleoprotein (RNP)–containing and RNP–depleted Matrices Analyzed by Sequential Fractionation and Resinless Section Electron Microscopy", *J. Cell. Biol.*, 102:1654–1665 (1986).

Fey and Penman, "Nuclear Matrix Proteins Reflect Cell Type of Origin in Cultured Human Cells", *Proc. Natl. Acad. Sci.*, 85:121–125 (1988).

Fey et al., "The Nuclear Matrix: Defining Structural and Functional Roles", *Crit. Rev. Euk. Gene Express*, 1:127–143 (1991).

Gerace et al., "Immunocytochemical Localization of the Major Polypeptides of the Nuclear Pore Complex–Lamina Fraction", *J. Cell. Biol.*, 79:546–566 91978).

Gerace and Burke, "Functional Organization of the Nuclear Envelope", *Ann. Rev. Cell Biol.*, 4:355–374 (1988).

Getzenberg and Coffey, "Tissue Specificity of the Hormonal Response in Sex Accessory Tissues is Associated with Nuclear Matrix Protein Patterns", *Mol. Endocrinol.*, 4:1336–1342 (1990).

(List continued on next page.)

*Primary Examiner*—Toni R. Scheiner
*Attorney, Agent, or Firm*—Testa, Hurwitz & Thibeault, LLP

[57] ABSTRACT

The invention provides methods and compositions for identifying colon cancers in an individual. In one embodiment of the invention, a colon adenocarcinoma-associated protein may be detected in a tissue or body fluid sample of an individual, to provide an indication of the presence of an adenocarcinoma of the colon in the individual. The target adenocarcinoma-associated protein, may be detected, e.g., by reacting the sample with a labeled binding moiety, such as a labeled antibody, capable of specifically binding the protein. In another embodiment, the protein may be detected by isolating one or more colon adenocarcinoma-associated proteins from the sample, separating the proteins by two dimensional gel electrophoresis, and comparing the gel electrophoresis pattern with a standard. The invention provides a wide range of assay methods and compositions which may be used for detecting colon tumors in an individual rapidly and reproducibly, optimally at early stages of the disease.

17 Claims, 4 Drawing Sheets

OTHER PUBLICATIONS

Getzenberg et al., "Identification of nuclear Matrix Proteins in the Cancer Normal Rate Prostate", *Cancer Res.,* 51:6514–6520 (1991).

Greenfield et al., "Human Papillomavirus 16 E7 Protein is Associated with the Nuclear Matrix", *Proc. Natl. acad. Sci.,* 88:11217–11221 (1991).

Gryska et al., "Screening Asymptomatic Patients at High Risk For Colon Cancer with Full Colonoscopy", *Dis. Colon Rectum,* 30:18–20 (1987).

Kaufman et al., "Characterization of the Major Polypeptides of the Rat Liver Nuclear Envelope", *J. Biol. Chem.,* 258:2710–2719 (1983).

Khanuja et al., "Nuclear Matrix Proteins in Normal and Breast Cancer Cells", *Cancer Res.,* 53:3394–3398 (1993).

Miller et al., "Detection of Nuclear Matrix Proteins in Serum from Cancer Patients", Cancer Research, 52:422–427 (1992).

Moertel et al., "An Evaluation of the Carcinoembryonic Antigen (CEA) Test for Monitoring Patients with Resected Colon Cancer", *J. Am. Med. Assoc.,* 270:943–947 (1993).

Oakley et al., "A Simplified Ultrasensitive Silver Stain for Detecting Proteins in Polyacrylamide Gels", *Anal Biochem.,* 105:361–363 (1980).

O'Farrell, "Nuclear Envelope Organization", *J. Biol. Chem.,* 250:4007–4021 (1975).

Ogata, N., "Preferential Association of a Transcriptionally Active Gene with the Nuclear Matrix of Rat Fibroblasts Transformed by a Simian–Virus–40–pBR322 Recombinant Plasmid", *Biochem. J.,* 267:385–390 (1990).

Olson and Miller, "Elsei 4: Quantitative Computer Analysis of Sets of Two–Dimensional Gel Electrophoretograms", *Anal. Biochem.,* 169:49–70 (1980).

Partin et al., "Nuclear Matrix Protein Pattern in Human Benign Prostatic Hyperplasia and Prostate Cancer", *Cancer Res.,* 53:744–746 (1993).

Pienta and Coffey, "A Structural Analysis of the Role of the Nuclear Matrix and DNA Loops in the Organization of the Nucleus and Chromosome", *J. Cell. Sci. Suppl.,* 1:123–125 (1984).

Stuurman et al., "The Nuclear Matrix from Cells of Different Orgin", *J. Biol. Chem.,* 265:5460–5465 (1990).

Vogelstein et al., "Genetic Alterations During Colorectal–Tumor Development", *N. Engl. J. Med.,* 319:525–532 (1988).

von Kries et al., "A Matrix/Scaffold Attachment Region Binding Protein: Identification, Purification, And Mode of Binding", *Cell,* 64:123–135 (1991).

Winawer et al., "Colorectal Cancer Screening", *J. Natl. Cancer Inst.,* 83:243–253 (1991).

Zeitlin et al., "Pre–mRNA Splicing and the Nuclear Matrix", *Mol. Cell. Biol.,* 7:111–120 (1987).

Zeitlin et al., "Autonomous Splicing and Complementation of In Vivo–Assembled Spliceosomes", *J. Cell. Biol.,* 108:765–777 (1989).

Hincks, J.R. et al., *Proceedings of American Association for Cancer Research,* 30:558 (1989).

Chiu, J–F et al., *Oncology* (Basel), 42(1):26–32 (1985) (Abstract only).

Melhem, M.F. et al., *Cancer Research,* 52:5853–5864 (1992).

Wen, G–G et al., *International Journal of Biochemistry,* 19(4):321–328 (1987).

METHODS AND COMPOSITIONS FOR THE DETECTION OF COLON CANCERS

This is a divisional of application(s) Ser. No. 08/168,993 filed on Dec. 17, 1993 now U.S. Pat. No. 5,547,928.

BACKGROUND OF THE INVENTION

Colon cancer is the second leading cause of cancer related deaths in the United States and other Western countries. Unlike lung cancer, for example, in which smoking has been identified as the prime etiologic factor responsible for the disease, the principle mechanisms underlying colon cancer are complex and incompletely understood. Dietary factors are believed to promote carcinogenesis, especially a high fat intake. Weisburger and Wynder, in *Important Advances in Oncology* (DeVita et al., eds., Lippincott, Philadelphia, Pa.), pp. 197–221 (1987); and Greenwald and Witkin, in *Frontiers of Gastrointestinal Research* (Rozen et al., eds., Karger, Basel), pp. 25–37 (1991). At the molecular level, a multi-step process involving a number of mutations is suspected in the progression to colon tumors. Vogelstein et al., *N. Engl. J. Med.*, 319:525–532 (1988); and Fearon and Vogelstein, *Cell*, 61:759–767 (1990).

Although carcino-embryonic antigen (CEA) is elevated in most advanced colon cancers, it is not an effective indicator of early disease or disease recurrence. Moertel, *J. Am. Med. Assoc.*, 270:943–947 (1993). The currently recommended method of screening for preneoplastic and stage I lesions is sigmoidoscopy with polyp removal and biopsy. Winawer et al., *J. Natl. Cancer Inst.*, 83:243–253 (1991); and Gryska and Cohen, *Dis. Colon Rectum*, 30:18–20 (1987). This is an invasive technique which incurs considerable discomfort to the patient. The identification of a tumor marker reliably detecting early disease or providing early prognostic information could lead to a diagnostic assay that would greatly aid in the management of this disease.

All eucaryotic cells have a nucleus containing DNA, or chromatin, which is organized by an internal protein scaffolding known as the nuclear matrix (NM). The nuclear matrix was first described in 1974 by Berezney and Coffey. Berezney and Coffey, *Biochem. Biophys. Res. Commun.*, 60:1410–1417 (1974). Penman and Fey disclose a method for selectively extracting insoluble interior nuclear matrix proteins and their associated nucleic acids from cells and determining the particular cell type by analyzing the proteins by two-dimensional gel electrophoresis. U.S. Pat. No. 4,882,268, issued Nov. 21, 1989, and U.S. Pat. No. 4,885,236, issued Dec. 5, 1989.

The nuclear matrix is believed to be involved in a wide variety of nuclear functions fundamental to the control of gene expression (For a general review see, for example, Fey et al. (1991) *Crit. Rev. Euk. Gene Express* 1:127–143). Tissue-specific nuclear matrix proteins have been identified in the rat, mouse and human. Fey and Penman, *Proc. Natl. Acad. Sci.*, 85:121–125 (1988); Stuurman et al., *J. Biol. Chem.*, 265:5460–5465 (1990); and Getzenberg and Coffey, *Mol. Endocrinol.*, 4:1336–1342 (1990). Changes in the presence or absence of specific nuclear matrix proteins have been associated with cellular transformation and differentiation. Bidwell et al., *Proc. Natl. Acad. Sci*, 90:3162–3166 (1993); Brancolini and Schneider, *Proc. Natl. Acad. Sci.*, 88:6936–6940 (1991); and Greenfield et al., *Proc. Natl. Acad. Sci.*, 88:11217–11221 (1991). Tumor-specific nuclear matrix proteins have been demonstrated in cancers of human and rat prostates (Partin et al., *Cancer Res.*, 53:744–746 (1993); and Getzenberg et al., *Cancer Res.*, s51:6514–6520 (1991)) and breast (Khanuja et al., *Cancer Res.*, 53:3394–3398 (1993)). Molecular characterization of the specific proteins of the nuclear matrix, however, remains poorly defined, due to the low abundance of these proteins in the cell and their generally insoluble character.

It is an object of this invention to provide colon tumor-associated molecules which are useful as markers for the rapid detection of colon tumors in an individual. It is another object of this invention to provide methods for detecting colon tumors in an individual at early stages of the disease. It is still another object of the invention to provide therapeutic methods and compositions for treating colon cancers in an individual. It is a further object of the invention to provide methods and compositions for monitoring the effect of the therapeutic treatment of colon cancers in an individual. These and other objects and features of the invention will be apparent from the description, figures and claims which follow.

SUMMARY OF THE INVENTION

The invention provides methods and compositions which permit the rapid and reproducible detection of the presence of a colon cancer in a mammal. In one embodiment, the invention provides isolated target colon adenocarcinoma-associated proteins, which may be detected in a tissue or body fluid sample of a mammal, to provide an indication of the presence of an adenocarcinoma of the colon in the mammal. To enhance the accuracy of the assay, a plurality of colon adenocarcinoma-associated proteins may be detected in the assay. The colon adenocarcinoma-associated protein may be detected in any of a wide range of possible mammalian body fluid or tissue samples. The protein may be detected, e.g., in a human body tissue sample, such as a colon tissue sample. Alternatively, the protein may be detected in a human body fluid sample, such as blood, serum, plasma, fecal, urine, semen, vaginal secretion, spinal fluid, saliva, ascitic fluid, peritoneal fluid, sputum, tissue swab, or a body exudate, such as breast exudate.

In another embodiment of the invention, the target protein detected in a tissue or body fluid sample may be associated with a metastasized adenocarcinoma of the colon. In this embodiment, detection of the protein thus provides an indication of the presence of a metastasized adenocarcinoma of the colon in the mammal. As used herein, the term "colon adenocarcinoma-associated" molecules refers to target molecules originating from and isolable from a colon adenocarcinoma, and substantially neither originating from nor isolable from normal colon cells. It is not necessary that the target molecule be unique to a colon adenocarcinoma cell. Rather, it is preferred that the target molecule have a signal to noise ratio high enough to discriminate between samples originating from colon tumor tissue and samples originating from normal colon tissue.

The accuracy of the tissue or body fluid assay may be further enhanced by detecting the absence in the sample of a protein associated with normal colon cells, and not associated with colon adenocarcinoma cells, thereby to confirm the presence of the colon adenocarcinoma. Conversely, in the assay, the presence of proteins associated with normal colon tissue, and the absence of proteins associated with a colon adenocarcinoma can serve as an indication of the absence of a colon adenocarcinoma in the individual being tested. The colon adenocarcinoma-associated or normal colon cell-associated protein may comprise, in one embodiment, a nuclear matrix protein, such as an interior nuclear matrix protein. The isolation of nuclear matrix proteins from cells is described in U.S. Pat. No. 4,882,268, issued Nov. 21, 1989, and U.S. Pat. No. 4,885,236, issued Dec. 5, 1989, the disclosures of which are incorporated herein by reference.

Target proteins associated with a colon adenocarcinoma cell, or with a normal colon cell, in a tissue or body sample, may be detected using any of a number of assay methods available in the art. In one embodiment, the protein may be reacted with a binding moiety, such as antibody, capable of specifically binding the protein being detected. Binding moieties, such as antibodies, may be designed using methods available in the art, which interact specifically with the protein being detected. Optionally, in the assay, a labeled binding moiety may be utilized. In this embodiment, the sample is reacted with a labeled binding moiety capable of specifically binding the protein, such as a labeled antibody, to form a labeled complex of the binding moiety and the target protein being detected. Detection of the presence of the labeled complex then may provide an indication of the presence of an adenocarcinoma of the colon in the individual being tested.

In another embodiment, one or more target proteins in a sample may be detected by isolating the proteins from the sample, and then separating the proteins by two-dimensional gel electrophoresis, to produce a characteristic two-dimensional gel electrophoresis pattern. The gel electrophoresis pattern then may be compared with a standard. The standard may be obtained from a data base of gel electrophoresis patterns. Thus, in one embodiment, e.g., the invention provides gel electrophoresis patterns of colon adenocarcinoma-associated proteins which are useful in detecting a colon adenocarcinoma in an individual.

The target proteins may be isolated from the sample by any of a range of protein isolation methods, well known to those skilled in the art, such as affinity chromatography, to yield isolated proteins. As used herein, "isolated" is understood to mean substantially free of undesired, contaminating proteinaceous material. In another embodiment, the target protein may be isolated from a cell sample using the methods for isolating nuclear matrix proteins disclosed in U.S. Pat. No. 4,885,236, issued Dec. 5, 1989, and U.S. Pat. No. 4,882,268, issued Nov. 21, 1989, the disclosures of which are incorporated herein by reference. In the isolation procedure, mammalian cells are extracted with an extracting solution comprising protease inhibitors, RNase inhibitors, and a non-ionic detergent-salt solution at physiological pH and ionic strength, to extract proteins in the nucleus and cytoskeleton which are soluble in the extracting solution. The target proteins then are separated from the cytoskeleton remaining in the extracted cells by solubilizing the cytoskeleton proteins in a solution comprising protease inhibitors and, e.g., a salt solution (such as 0.25M $(NH_4)_2SO_4$), which does not dissolve the target proteins. The chromatin then is separated from the target proteins by digesting the insoluble material with DNase, in a buffered solution containing protease inhibitors. The insoluble target proteins then are dissolved in a solubilizing agent, such as 8M urea, plus protease inhibitors, and dialyzed into a physiological buffer comprising protease inhibitors, wherein the target proteins are soluble in the physiological buffer, and insoluble proteins are removed from the solution.

In another embodiment, a nucleic acid molecule encoding the isolated target protein may be obtained by methods available in the art. For example, an isolated colon adenocarcinoma-associated protein may be sequenced using methods available in the art, and then oligonucleotide probes may be designed for screening a cDNA library. The cDNA library then may be screened to obtain the sequence of the nucleic acid molecule encoding for the isolated protein. (See, e.g., Maniatis et al., eds., "Molecular Cloning: A Laboratory Manual,"0 Cold Spring Harbor Press (1989)).

In another embodiment, a nucleic acid molecule may be isolated from a cell sample which comprises a sequence capable of recognizing and being specifically bound by a colon adenocarcinoma-associated protein. In yet another embodiment, the nucleic acid molecule may comprise a sequence capable of recognizing and being specifically bound by a protein associated with a metastasized adenocarcinoma of the colon. Detection of the nucleic acid molecule thus can serve as an indicator of the presence of a metastasized adenocarcinoma of the colon in the mammal. As used herein the term "specifically bound" refers to a binding affinity of greater than about $10^5$ $M^{-1}$.

In one embodiment, a nucleic acid molecule comprising a sequence capable of recognizing and being specifically bound by a colon adenocarcinoma-associated protein can be isolated according to the methods disclosed in U.S. Pat. No. 4,885,236, issued Dec. 5, 1989 and in U.S. Pat. No. 4,882,268, issued Nov. 21, 1989. In this procedure, the soluble proteins are separated from the nucleus and cytoskeleton by extracting mammalian cells with a non-ionic detergent solution at physiological pH and ionic strength. The insoluble protein and nucleic acids then are digested with DNase and then eluted with a buffered ammonium sulfate solution to yield a nucleic acid molecule capable of recognizing and being specifically bound by a colon adenocarcinoma-associated protein. Any remaining proteins then are separated from the target nucleic acid molecule.

A target nucleic acid molecule in a sample may be detected by, e.g., a northern blot analysis by reacting the sample with a labeled hybridization probe, wherein the probe is capable of hybridizing specifically with at least a portion of the target nucleic acid molecule. Detection of the target nucleic acid molecule in a sample, encoding or capable of being specifically bound by a colon tumor-associated protein, thus can serve as an indicator of the presence of a colon adenocarcinoma in the individual being tested.

Thus, the invention provides a wide range of methods and compositions for detecting a colon cancer in an individual. In one embodiment, the invention provides colon adenocarcinoma-associated proteins and nucleic acids, as well as methods for their use, which permit a colon adenocarcinoma in an individual to be rapidly detected, preferably before metastasis of the tumor can occur. The invention provides methods for detecting colon adenocarcinomas and for monitoring of the efficacy of therapeutic treatments. Using the methods and compositions disclosed herein, adenocarcinomas of the colon can be detected in individuals to permit treatment at early stages of the disease. In a further embodiment, the invention provides methods and compositions which may be used in the therapeutic treatment of colon tumors.

DETAILED DESCRIPTION

I. GENERAL

The invention provides a wide range of methods and compositions for detecting the presence of a colon cancer in an individual. In one embodiment, the invention provides colon adenocarcinoma-associated proteins and nucleic acid molecules, which may be detected in a tissue or body fluid sample of a mammal, e.g., in cellular or extracellular fluid, to provide an indication of the presence of an adenocarcinoma of the colon in the mammal. As used herein, the term "colon adenocarcinoma-associated" molecules refers to molecules originating from and isolable from a colon adenocarcinoma. The discussion of the isolation and detection of colon adenocarcinoma-associated molecules herein is exemplary. The isolation and detection of molecules associated with other types of colon cancer cells, such as sarcomas, is readily within the scope of the invention.

The presence of a protein or nucleic acid molecule in a tissue or body fluid sample of an individual can be rapidly and reproducibly detected using the methods and compositions disclosed herein. In one embodiment, a protein or nucleic acid molecule may be detected in a tissue or body fluid sample which is associated with a metastasized adenocarcinoma of the colon. To enhance the accuracy of the assay, a plurality of colon adenocarcinoma-associated proteins may be detected in the sample. The accuracy of the assay may be further enhanced by detecting in the tissue or body fluid sample of the mammal the absence of protein associated with normal colon cells, and not associated with colon adenocarcinoma cells, to confirm the presence of the colon adenocarcinoma in the mammal. Thus, the invention provides a wide range of compositions and methods which are useful in diagnosing colon cancers in an individual.

In one embodiment, the invention provides the six colon adenocarcinoma-associated proteins, designated CC-1 through CC-6, listed in Table 1. In another embodiment, the invention provides the four proteins associated with normal colon cells, and not associated with colon adenocarcinoma cells, designated NC-1 through NC-4, listed in Table 2. The proteins listed in Tables 1 and 2 may be isolated, e.g., using the methods disclosed in U.S. Pat. No. 4,882,268, issued Nov. 11, 1989, and U.S. Pat. No. 4,885,236, issued Dec. 5, 1989. The approximate molecular weight and isoelectric point for each of the proteins is listed in Tables 1 and 2. The isoelectric point was determined using standard isoelectric focusing techniques, and the molecular weight was determined using standard polyacrylamide gel electrophoresis techniques. The molecular weights ($M_r$) listed in Tables 1 and 2 are approximate, and represent values which are accurate to within approximately ±1,000 daltons. The isoelectric point (pI) values in Tables 1 and 2 are accurate to within approximately ±0.2 pH units. The isolation and characterization of the proteins listed in Tables 1 and 2 are described in detail in Section III.

TABLE 1

| Protein | $M_r$ | pI | Normal (n = 10) | Cancer (n = 18) |
|---|---|---|---|---|
| CC*-1 | 22,359 | 6.6 | − | + |
| CC-2  | 23,505 | 6.9 | − | + |
| CC-3  | 20,838 | 6.7 | − | + |
| CC-4  | 26,477 | 6.3 | − | + |
| CC-5  | 26,000 | 7.2 | − | + |
| CC-6  | 58,600 | 6.6 | − | + |

*Colon Cancer

TABLE 2

| Protein | $M_r$ | pI | Normal (n = 10) | Cancer (n = 18) |
|---|---|---|---|---|
| NC*-1 | 40,640 | 7.0 | + | − |
| NC-2  | 34,240 | 6.0 | + | − |
| NC-3  | 30,939 | 7.2 | + | − |
| NC-4  | 17,400 | 7.3 | + | − |

*Normal Colon

A. Therapeutic Applications

The invention provides a wide range of assay methods and compositions for detecting a colon adenocarcinoma in an individual. In one embodiment, the level of a colon-tumor associated protein, or a nucleic acid encoding it, or a nucleic acid capable of a binding interaction with it, may be monitored over time, to, e.g., evaluate the status of a disease or the efficacy of a therapeutic treatment or procedure (such as a chemotherapeutic agent or radiation treatment.) In another embodiment, the isolated colon-tumor associated proteins, the nucleic acid sequences encoding them, or the nucleic acids capable of a binding interaction with them, may be used as target molecules in therapeutic procedures, to inhibit or disable the tumor cell's ability to undergo cell division.

The colon tumor-associated proteins disclosed herein, in one embodiment, comprise nuclear matrix proteins, isolable, e.g., by the methods disclosed in U.S. Pat. No. 4,882,268, issued Nov. 11, 1989. The nuclear matrix is believed to be involved in a wide variety of nuclear functions fundamental to gene expression. (See, e.g., Fey et al., *Crit. Rev. Euk. Gene Express* 1:127–143 (1991)). Accordingly, without being limited to any particular theory, it is hypothesized that isolated colon adenocarcinoma-associated proteins originating from the nuclear matrix likely play a significant role, e.g., a structurally or functionally related role. Accordingly, these proteins and their transcripts are good candidates as target molecules for a cancer chemotherapy. The sequence of the isolated proteins, as well as the sequence of the nucleic acid transcripts encoding for them, can be readily determined using methods available in the art. (See, e.g., Maniatis et al., eds., "Molecular Cloning: A Laboratory Manual," Cold Spring Harbor Press, (1989)).

A particularly useful cancer therapeutic envisioned is an oligonucleotide complementary to part all of the target protein transcript, capable of hybridizing specifically to the transcript and inhibiting translation of the mRNA when hybridized to the mRNA transcript. These complementary sequences are known in the art as "antisense" sequences, and can be synthesized chemically or by standard recombinant DNA techniques using methods available in the art. The antisense oligonucleotides can be chemically modified to enhance their stability. Antisense oligonucleotides have been used extensively to inhibit gene expression in normal and abnormal cells. See, for example, Stein et al., *Cancer Res.*, 48:2659–2668 (1988), for a pertinent review of antisense therapy and established protocols. The antisense therapy may be used in cancer chemotherapy, either alone or in combination with other therapies. Methods for antisense therapy are also described in U.S. Ser. No. 07/901,701, filed Jun. 22, 1992, the disclosure of which is incorporated herein by reference.

In another embodiment, a binding protein designed to bind the colon tumor-associated protein essentially irreversibly can be provided to the malignant cells, e.g., by association with a ligand specific for the cell and known to be absorbed by the cell. Means for targeting molecules to particular cells and cell types are well described in the chemotherapeutic art.

II. SPECIFIC EMBODIMENTS

A. Protein Isolation

A target protein, associated with colon adenocarcinoma cells, or associated with normal colon cells, can be isolated using standard methodologies well known to those of ordinary skill in the art, such as affinity chromatography, to yield substantially pure proteins. As used herein, "isolated" is understood to mean substantially free of undesired, contaminating proteinaceous material. The target proteins may also be isolated, e.g., by the methods for isolating nuclear matrix proteins disclosed in U.S. Pat. Nos. 4,882,268 issued Nov. 11, 1989 and 4,885,236, issued Dec. 5, 1989, the disclosures of which are incorporated herein by reference.

B. Protein Detection Methods

A target protein, associated with a colon adenocarcinoma, or with normal colon cells, may be detected in a sample using any of a range of binding assays well known to those of ordinary skill in the art. In one embodiment, the target protein in a sample may be reacted with a binding moiety capable of specifically binding the target protein. The binding moiety may comprise, e.g., a member of a ligand-receptor pair, i.e., a pair of molecules capable of specific binding interactions. The binding moiety may comprise, e.g., a member of a specific binding pair, such as antibody-antigen, enzyme-substrate, nucleic acid-nucleic acid, protein-nucleic acid, or other specific binding pairs known in the art. Binding proteins may be designed which have enhanced affinity for a target protein. Optionally, the binding moiety may be linked with a detectable label, such as an enzymatic, fluorescent, radioactive, phosphorescent or colored particle label. The labeled complex may be detected, e.g., visually or with a spectrophotometer or other detector.

The proteins also may be detected using gel electrophoresis techniques available in the art, as disclosed, e.g., in Maniatis et al., eds., "Molecular Cloning: A Laboratory Manual," Cold Spring Harbor Press, (1989). In one embodiment, one or more target proteins may be detected by isolating the proteins from a sample, and then separating the proteins by two-dimensional gel electrophoresis, to produce a characteristic two-dimensional gel electrophoresis pattern, and comparing the gel electrophoresis pattern with a standard gel pattern derived from normal or cancer cells and run under identical conditions. The standard may be stored or obtained in an electronic database of electrophoresis patterns. In two-dimensional gel electrophoresis, the proteins are first separated in a pH gradient gel according to their isoelectric point. This gel then is placed on a polyacrylamide gel, and the proteins are separated according to molecular weight. (See, e.g., O'Farrell, *J. Biol. Chem.* 250: 4007–4021 (1975)).

B.1. Immunoassays

A target adenocarcinoma-associated, or normal colon cell-associated protein in a sample may be detected using any of a wide range of immunoassay techniques available in the art. In one embodiment, a sandwich immunoassay technique may be utilized. In this method, two antibodies capable of binding the target protein generally are used: e.g., one immobilized onto a solid support, and one free in solution and labeled with detectable chemical compound. Examples of chemical labels that may be used for the second antibody include radioisotopes, fluorescent compounds, and enzymes or other molecules which generate colored or electrochemically active products when exposed to a reactant or enzyme substrate. When a sample containing the target protein is placed in this system, the target protein binds to both the immobilized antibody and the labeled antibody, to form a "sandwich" immune complex on the support's surface. The complexed protein is detected by washing away non-bound sample components and excess labeled antibody, and measuring the amount of labeled antibody complexed to protein on the support's surface.

The sandwich immunoassay is highly specific and very sensitive, provided that labels with good limits of detection are used. A detailed review of immunological assay design, theory and protocols can be found in numerous texts in the art, including *Practical Immunology*, Butt, W. R., ed., Marcel Dekker, New York, 1984.

In general, immunoassay design considerations include preparation of antibodies (e.g., monoclonal or polyclonal) having sufficiently high binding specificity for the target protein to form a complex that can be distinguished reliably from products of nonspecific interactions. As used herein, "antibody" is understood to include other binding proteins having appropriate binding affinity and specificity for the target protein. The higher the antibody binding specificity, the lower the target protein concentration that can be detected. A preferred binding specificity is such that the binding protein has a binding affinity for the target protein of greater than about $10^5$ $M^{-1}$, preferably greater than about $10^7$ $M^{-1}$.

Antibody binding domains also may be produced biosynthetically and the amino acid sequence of the binding domain manipulated to enhance binding affinity with a preferred epitope on the target protein. Specific antibody methodologies are well understood and described in the literature. A more detailed description of their preparation can be found, for example, in *Practical Immunology*, Butt, W. R., ed., Marcel Dekker, New York, 1984. optionally, a monovalent antibody such as an Fab antibody fragment may be utilized. Additionally, genetically engineered biosynthetic antibody binding sites may be utilized which comprise either 1) non-covalently associated or disulfide bonded synthetic $V_H$ and $V_L$ dimers, 2) covalently linked $V_H$–$V_L$ single chain binding sites, 3) individual $V_H$ or $V_L$ domains, or 4) single chain antibody binding sites as disclosed, for example in Huston et al., U.S. Pat. No. 5,091,513 (1992) and U.S. Pat. No. 5,132,405 (1992), and in Ladner et al., U.S. Pat. No. 4,704,692 (1987) and U.S. Pat. No. 4,946,778 (1990), the disclosures of which are incorporated herein by reference.

B.2. Antibody Production

Antibodies to isolated target colon adenocarcinoma-associated or normal colon tissue-associated proteins which are useful in assays for detecting a colon adenocarcinoma in an individual may be generated using standard immunological procedures well known and described in the art. See, for example, *Practical Immunology*, Butt, N. R., ed., Marcel Dekker, New York, 1984. Briefly, an isolated target protein is used to raise antibodies in a xenogeneic host, such as a mouse, goat or other suitable mammal. Preferred antibodies are antibodies that bind specifically to an epitope on the protein, preferably having a binding affinity greater than $10^5$ $M^{-1}$, most preferably having an affinity greater than $10^7$ $M^{-1}$ for that epitope.

The protein is combined with a suitable adjuvant capable of enhancing antibody production in the host, and injected into the host, for example, by intraperitoneal administration. Any adjuvant suitable for stimulating the host's immune response may be used to advantage. A commonly used adjuvant is Freund's complete adjuvant (an emulsion comprising killed and dried microbial cells, e.g., from Calbiochem Corp., San Diego, or Gibco, Grand Island, N.Y.). Where multiple antigen injections are desired, the subsequent injections comprise the antigen in combination with an incomplete adjuvant (e.g., cell-free emulsion).

Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target protein and have the desired binding affinity.

Provided below is an exemplary protocol for monoclonal antibody production, which is currently preferred. Other protocols also are envisioned. Accordingly, the particular method of producing antibodies to target proteins is not envisioned to be an aspect of the invention.

Exemplary antibody production protocol

Antibodies to a target protein may be readily prepared using methods available in the art. In one embodiment, Balb/c by J mice (Jackson Laboratory, Bar Harbor, Me.) are injected intraperitoneally with the target protein (e.g., a colon tumor-associated protein isolated from the colon tumor cell line Caco) every 2 weeks for a total of 16 weeks. The mice are injected with 3 consecutive intravenous boosts, 3 days prior to sacrifice and removal of the spleen. Freund's complete adjuvant (Gibco, Grand Island) is used in the first injection, incomplete Freund's in the second injection; subsequent injections are made with saline. Spleen cells (or lymph node cells) then are fused with a mouse myeloma line, e.g., using the method of Kohler and Milstein, *Nature*, 256:495 (1975), the disclosure of which is incorporated herein by reference, and using polyethylene glycol (PEG, Boehringer Mannheim, Germany). Hybridomas producing antibodies that react with the target proteins then are cloned and grown as ascites. Hybridomas are screened by nuclear reactivity against the cell line that is the source of the immunogen, and by tissue immunohistochemistry using standard procedures known in the immunology art. Detailed descriptions of screening protocols, ascites production and immunoassays also are disclosed in U.S. Ser. No. 08/112,646, filed Aug. 26, 1993, the disclosure of which is incorporated herein by reference.

C. Nucleic Acid Assays

The presence of a colon tumor in an individual also ay be determined by detecting, in a tissue or body fluid sample, a nucleic acid molecule encoding a colon tumor-associated-protein. Using methods well known to those of ordinary skill in the art, the colon tumor-associated or normal colon-tissue associated proteins of the invention may be sequenced, and then, based on the determined sequence, oligonucleotide probes may be designed for screening a cDNA library to determine the sequence of a nucleic acids encoding for the target proteins. (See, e.g., Maniatis et al., eds., "Molecular Cloning: A Laboratory Manual," Cold Spring Harbor Press, (1989)).

A target nucleic acid molecule, encoding an adenocarcinoma-associated protein, may be detected using a binding moiety, optionally labeled, capable of specifically binding the target nucleic acid. The binding moiety may comprise, e.g., a protein or a nucleic acid. Additionally, a target nucleic acid, such as an mRNA encoding a colon adenocarcinoma-associated protein, may be detected by conducting a northern blot analysis using labeled oligonucleotides, e.g., nucleic acid fragments complementary to and capable of hybridizing specifically with at least a portion of a target nucleic acid. While any length oligonucleotide may be utilized to hybridize an mRNA transcript, oligonucleotides typically within the range of 8–100 nucleotides, preferably within the range of 15–50 nucleotides, are envisioned to be most useful in standard RNA hybridization assays.

The oligonucleotide selected for hybridizing to the target nucleic acid, whether synthesized chemically or by recombinant DNA, is isolated and purified using standard techniques and then preferably labeled (e.g., with $^{35}$S or $^{32}$P) using standard labeling protocols. A sample containing the target nucleic acid then is run on an electrophoresis gel, the dispersed nucleic acids transferred to a nitrocellulose filter and the labeled oligonucleotide exposed to the filter under suitable hybridizing conditions, e.g. 50% formamide, 5× SSPE, 2×Denhardt's solution, 0.1% SDS at 42° C., as described in Maniatis et al., eds., "Molecular Cloning: A Laboratory Manual," Cold Spring Harbor Press, (1989). Other useful procedures known in the art include solution hybridization, and dot and slot RNA hybridization. The amount of the target nucleic acid present in a sample then optionally is quantitated by measuring the radioactivity of hybridized fragments, using standard procedures known in the art.

Following a similar protocol, oligonucleotides also may be used to identify other sequences encoding members of the target protein families. The methodology also may be used to identify genetic sequences associated with the nucleic acid sequences encoding the proteins described herein, e.g., to identify non-coding sequences lying upstream or downstream of the protein coding sequence, and which may play a functional role in expression of these genes. Additionally, binding assays may be conducted to identify and detect proteins capable of a specific binding interaction with a nucleic acid encoding a colon adenocarcinoma-associated protein, which may be involved e.g., in gene regulation or gene expression of the protein. In a further embodiment, the assays described herein may be used to identify and detect nucleic acid molecules comprising a sequence capable of recognizing and being specifically bound by a colon adenocarcinoma-associated protein.

III. EXEMPLIFICATION

The following examples describe the isolation of the colon adenocarcinoma-associated proteins from colon tumor tissue as well as a panel of different colon tumor cell lines. Additionally, the isolation of proteins associated with normal colon tissue, and not associated with colon adenocarcinoma tissue is described. The proteins were isolated essentially following the method of Penman and Fey, described in U.S. Pat. Nos. 4,882,268 and 4,885,236, the disclosures of which are herein incorporated by reference.

A. Tissue Samples

Fresh colon tumor or normal adjacent tissue samples were obtained under IRB approval from the Cooperative Human Tissue Network (CHTN, Columbus, Ohio) or AntiCancer, Inc. (San Diego, Calif.) from patients undergoing partial colectomy for clinically localized (Stage II or III, AJCC/UICC Group Staging Criteria; Stage B or C, Dukes classification) adenocarcinoma of the colon. Normal colon tissues were obtained from fatally injured trauma victims through the International Institute for the Advancement of Medicine (IIAM) and from normal adjacent tissue (CHTN) in patients undergoing surgery for colon tumor resection.

Fresh tissue was obtained during surgery or before termination of life support and was placed into transport medium (RPMI (Roswell Park Memorial Institute) supplemented with gentamicin and 10% fetal calf serum, GIBCO) and shipped by overnight transfer at 4° C. Minimum size of tissue specimens was 0.5 g. Diagnosis was obtained from pathology reports which accompanied each specimen and was histologically confirmed with hematoxylin and eosin staining. For normal colon tissue, partial sections approximately 6 inches in length were processed. The epithelial mucosa was harvested from underlying muscularis propria by scraping prior to target protein extraction.

B. Cell Lines

DLD, LoVo, HT-29, COLO, Caco and SW-1116 colon tumor cell lines were commercially obtained from the American Type Culture Collection (ATCC) and maintained at 37° in 5% $CO_2$ in Dulbecco's Modified Eagles Medium supplemented with 10% fetal calf serum, gentamicin, fungizone and 0.12% SerXtend (Irvine Scientific, Irvine, Calif.). For protein extraction studies, cells were grown to 80% confluency, harvested by trypsinization, counted and replated in larger culture vessels until appropriate cell numbers were obtained.

C. Protein Purification

Target proteins, associated with colon tumor tissue, or normal colon tissue, were isolated by a modification of the method of Fey and Penman. Fey and Penman, *Proc. Natl. Acad Sci.*, 85:121–125 (1988). Normal or colon tumor tissue specimens were minced into small (1 $mm^3$) pieces and homogenized with a Teflon pestle on ice and treated with a buffered solution containing 0.5% Triton-X-100, vanadyl riboside complex (RNase inhibitor, Five Prime-Three Prime) plus a protease inhibitor cocktail (phenylmethyl sulfonyl fluoride, Sigma; and aprotinin and leupeptin, Boehringer Mannheim) to remove lipids and soluble proteins. Tumor cells were harvested by trypsinization and treated in the same way as homogenized tumor tissue. Stromal aggregates were removed by filtering the homogenate through a 250 micron nylon screen (Nitex, Tetko, Inc.) followed by a centrifugation step.

Soluble cytoskeletal proteins were removed by incubating the pellet in an extraction buffer containing 250 mM $(NH_4)_2SO_4$, 0.5% Triton-X-100, vanadyl riboside complex plus a protease inhibitor cocktail for 10 minutes on ice followed by centrifugation. Chromatin was removed by incubating the pellet in DNase I (100 micrograms per ml, Boehringer-Mannheim, Indianapolis, Ind.), in a buffered solution containing a protease inhibitor cocktail for 45 minutes at 25° C.

The remaining pellet fraction, containing the target proteins and intermediate filaments, was solubilized in a disassembly buffer containing 8M urea, protease inhibitor cocktail plus 1% 2-mercaptoethanol. Insoluble contaminants, primarily carbohydrates and extracellular matrix, were removed by ultracentrifugation. Intermediate filaments were allowed to reassemble upon removal of urea by dialysis in assembly buffer containing protease inhibitor cocktail and removed by ultracentrifugation, leaving the target proteins in the supernatant fraction. Protein concentrations were determined by the Coomassie Plus Protein Assay Kit (Pierce Chemicals, Rockford, Ill.) using a bovine gamma globulin standard. Proteins were immediately precipitated and stored at −80° C.

D. Two-Dimensional Gel Electrophoresis

Two-dimensional electrophoresis was carried out by Kendrick Labs, Inc. (Madison, Wis.) according to the methodology of O'Farrell. O'Farrell, *J. Biol. Chem.*, 250:4007–4021 (1975). Isoelectric focusing (IEF) was carried out in glass tubes of inner diameter 2.0 mm using 2.0% pH 4–8 ampholytes (BDH, Hoefer Scientific Instruments, San Francisco, Calif.) for 9600 volt-hours. Samples were solubilized for IEF in a buffer containing 9.5M urea, 2% NP-40, 5% 2-mercaptoethanol and 2% ampholytes. Forty nanograms of an internal standard protein, tropomyosin ($M_r$ 33,000, pI 5.2) were added to each sample. Following isoelectric focusing and equilibration for 10 minutes in a buffer containing 10% glycerol, 50 mM dithiothreitol, 2.3% SDS and 0.06M Tris, pH 6.8, tube gels were sealed to the top of a stacking gel which is placed on top of a 10% polyacrylamide slab gel.

SDS slab gel electrophoresis was then carried out for 4–5 hours at 12.5 mA per gel. The following proteins were added as molecular weight standards to the agarose used for sealing the tube gel to the slab gel: phosphorylase A ($M_r$ 94,000), catalase ($M_r$ 60,000), actin ($M_r$ 43,000), carbonic anhydrase ($M_r$ 29,000) and lysozyme ($M_r$ 14,000). Slab gels were fixed in a solution containing 10% acetic acid/50% methanol overnight. Gels were silver stained according to the method of Oakley et al. (Oakley, et al., *Anal. Biochem.*, 105:361–363 (1980)) and dried between two sheets of cellophane paper.

E. Image Analysis

Image analysis of silver stained 2-D gels was performed using a MasterScan Biological Imaging System (CSP Inc., Billerica, Mass.). Following the acquisition of quantitative, -high resolution images of gels, digital filtering algorithms were used to remove both uniform and non-uniform background without removing critical image data. Two-D scan™ two dimensional gel analysis and database software, version 3.1, using multiple Gaussian least-squares fitting algorithms, were used to compute spot patterns into optimal-fit models of the data. Olson and Miller, *Anal. Biochem.*, 169:49–70 (1980). Triangulation from internal standards was used to precisely determine the molecular weight and isoelectric point of each target protein of interest. Interpretive densitometry then was performed using specific software application modules to integrate the data into numeric and graphical reports for each gel being analyzed.

F. Identification of Colon Tumor and Normal Colon Associated Proteins

The 2-D gel electrophoresis patterns of proteins isolated from colon tumor tissue were compared to patterns proteins isolated from normal colon tissue. The tumor tissue samples were obtained from 18 patients undergoing surgery for presumed adenocarcinoma of the colon as described in Section III.A. Normal colon tissue samples (5 specimens from trauma victims and 5 normal adjacent tissues), also were obtained as described in Section III.A. Tables 3A and 3B summarize characteristics of the patient population. In all of the cancer patients, the tumor had invaded

TABLE 3A

Patient/Tumor Characteristics

| Patient No. | Age/Sex | Histopathological Diagnosis (Stage Grade*) | Positive Nodes** |
|---|---|---|---|
| 1 FT0002 | 61/M | Moderately differentiated/ ($T_3N_2$) | 5/11 |
| 2 FT0004 | 57/M | Well differentiated ($T_3N_0$) | 0/9 |
| 3 FT0006 | 78/M | Infiltrating mod. diff. ($T_2N_0G_2$) | 0/3 |
| 4 FT0008 | 66/M | Well differentiated ($T_3N_0G_1$) | 0/9 |
| 5 FT00I3 | 77/F | Invasive (Mod. Dukes C2) | 6/13 |
| 6 FT0015 | 82/F | Poorly differentiated (Mod. Dukes B2) | 0/19 |
| 7 FT0018 | 54/M | Mixed mod. diff./mucinous ($T_3N_2$) | 8/9 |
| 8 FT0029 | 76/M | Mod. diff., infiltrating (Mod. Dukes B2) | 0/16 |
| 9 FT0031 | 80/M | Poorly differentiated (Mod. Dukes D) | 5/9 |
| 10 FT0033 | 82/F | Infiltrating mod. diff. ($T_3N_1G_2$) | 1/10 |

*1987 AJCC/UICC Staging Classification
**Number of positive lymph nodes/number biopsied

TABLE 3B

Patient/Tumor Characteristics

| Patient No. | Age/Sex | Histopathological Diagnosis (Stage Grade*) | Positive Nodes** |
|---|---|---|---|
| 11 FT0050 | 74/F | Infiltrating mod. diff. (Mod. Dukes B2) | 0/9 |
| 12 FT0054 | 75/F | Invasive mod. diff. (Mod. Dukes C2) | 2/12 |
| 13 FT0056 | 69/M | Infiltrating well diff. ($T_3N_0$) | 0/34 |
| 14 FT0080 | 43/F | Mod. differentiated ($T_3N_0$) | 0/21 |
| 15 FT0096 | 63/M | Mod. invasive diff. (Mod. Dukes B1) | 0/16 |
| 16 FT0098 | 67/M | Mod. differentiated ($T_3N_0$) | 0/8 |
| 17 FT0101 | 47/F | Mod. invasive diff. (Mod. Dukes B1) | 0/8 |
| 18 FT0110 | 75/F | Mod. well differentiated ($T_3N_0$) | 0/52 |

*1987 AJCC/UICC Staging Classification
**Number of positive lymph nodes/number biopsied the muscularis propia. The majority of the tumors were moderately differentiated, with proximal lymph node involvement reported in 6 of 18 cases.

Figure 1:
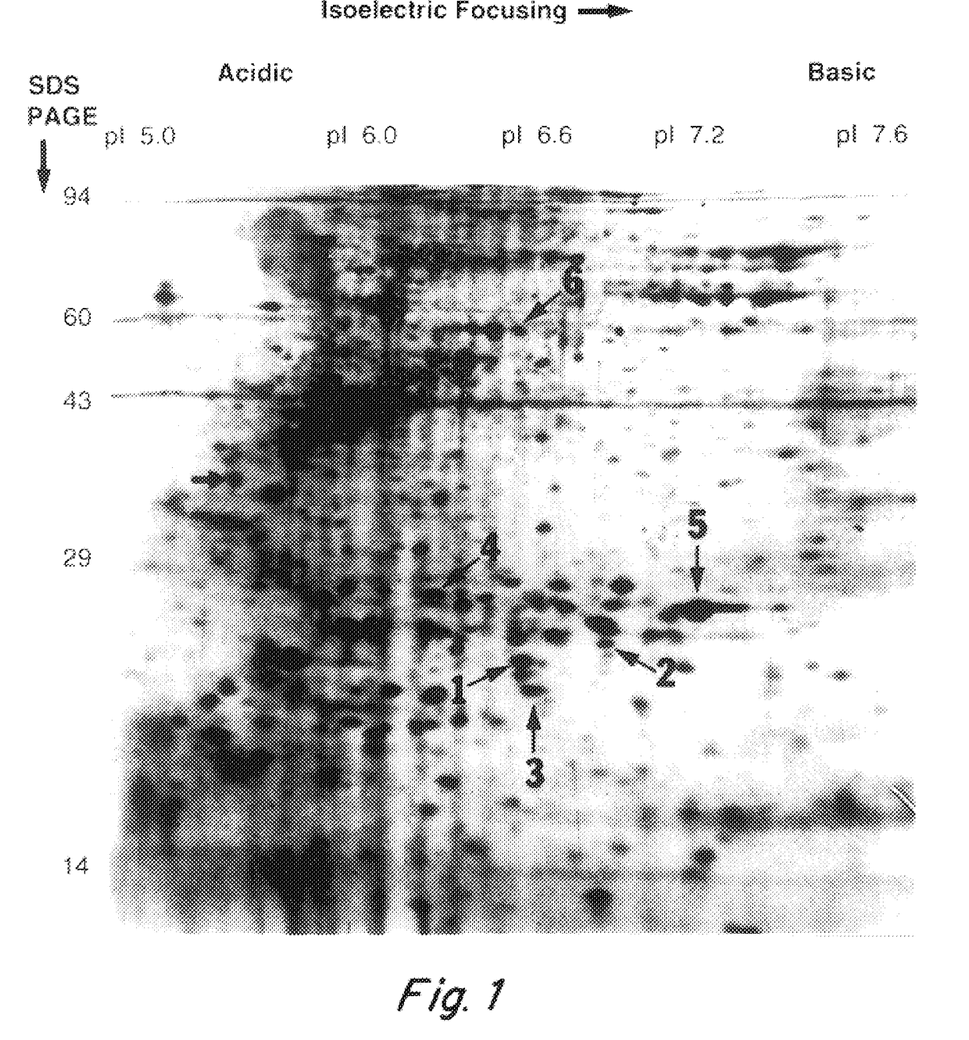
FIG. 1 is a high resolution two-dimensional gel electrophoresis pattern of colon adenocarcinoma-associated proteins isolated from a colon tumor tissue sample.
Figure 2:
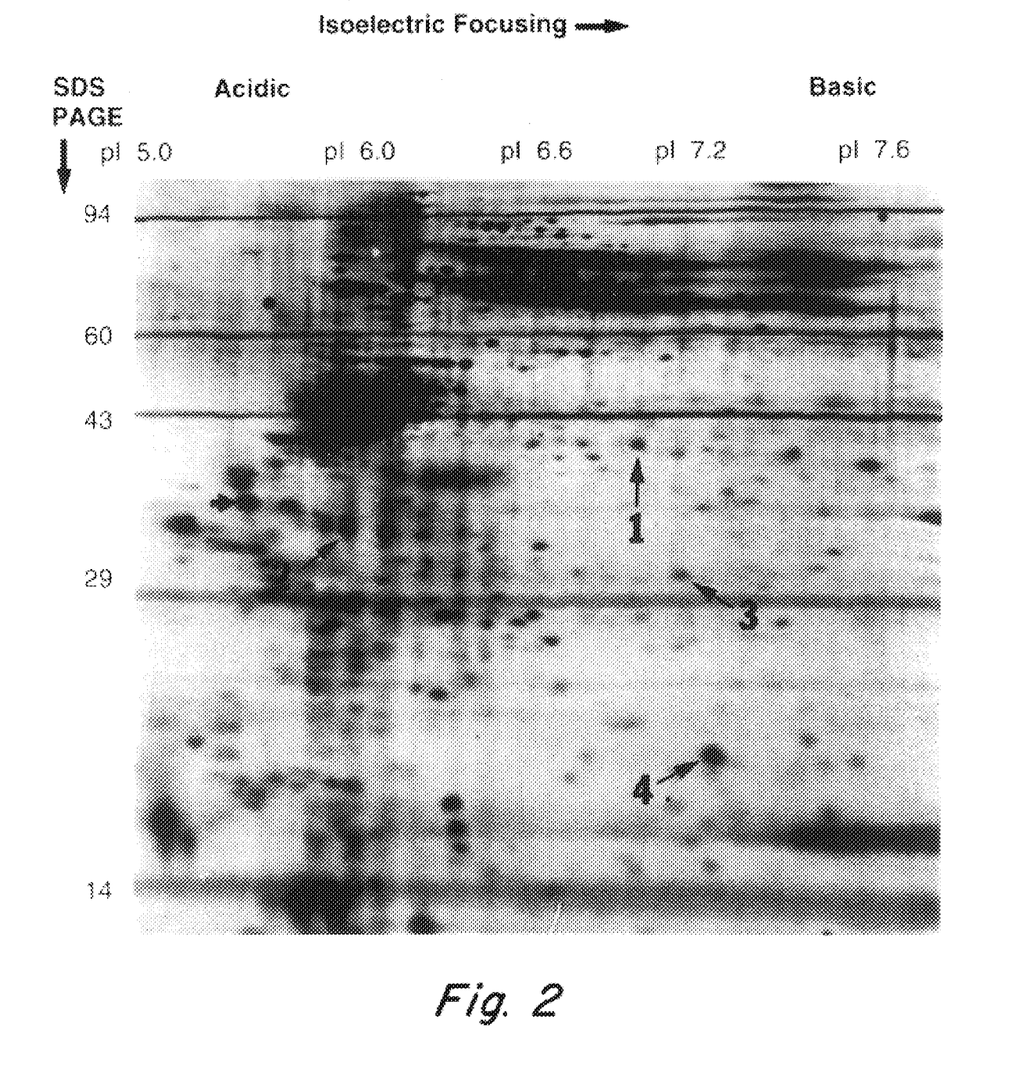
FIG. 2 is a high resolution two-dimensional gel electrophoresis pattern of proteins associated with normal colon cells, and isolated from normal colon tissue.

The isolated proteins from normal and colon cancer tissue were analyzed using high resolution two-dimensional (2-D) gel electrophoresis, as described in Section III.D-E. Approximately 500 proteins could be identified per gel. FIG. 1 is a high resolution 2-D gel electrophoresis pattern of isolated proteins from a colon cancer tissue sample. FIG. 2 is a high resolution 2-D gel electrophoresis pattern of proteins isolated from a normal colon tissue sample. In FIGS. 1 and 2, molecular weight standards are represented on the ordinate in thousands, while the isoelectric point is represented in the abscissa in pH units.

Comparison of 2-D gel electrophoresis patterns of proteins isolated from colon cancer tissue (FIG. 1) with patterns of proteins isolated from normal colon tissue (FIG. 2), revealed that while most of the proteins are found in both normal and malignant tissue, a small number were found that were consistently present substantially only in tumors or in normal tissue. At least 6 proteins were expressed in 18/18 tumors but 0/10 normal tissues (FIG. 1 and Table 1). Table 1 lists these colon adenocarcinoma-associated proteins, designated CC-1–CC-6, as well as their determined approximate molecular weights and isoelectric points. The colon tumor associated proteins are identified in FIG. 1 with arrows numbered 1–6 which correspond to proteins CC-1 to CC-6 listed in Table 1.

Additionally, at least four proteins were found to be present in all 10 normal colon tissue samples, and absent in colon cancer tissue (FIG. 2 and Table 2). These proteins are identified in FIG. 2 with arrows numbered 1–4, and are listed in Table 2 as proteins NC-1 to NC-4. The molecular weights ($M_r$) listed in Tables 1 and 2 are approximate, and represent values which are accurate to within approximately ±1,000 daltons. The isoelectric point (pI) values in Tables 1 and 2 also are approximate and are accurate to within approximately ±0.2 pH units.

Figure 3:
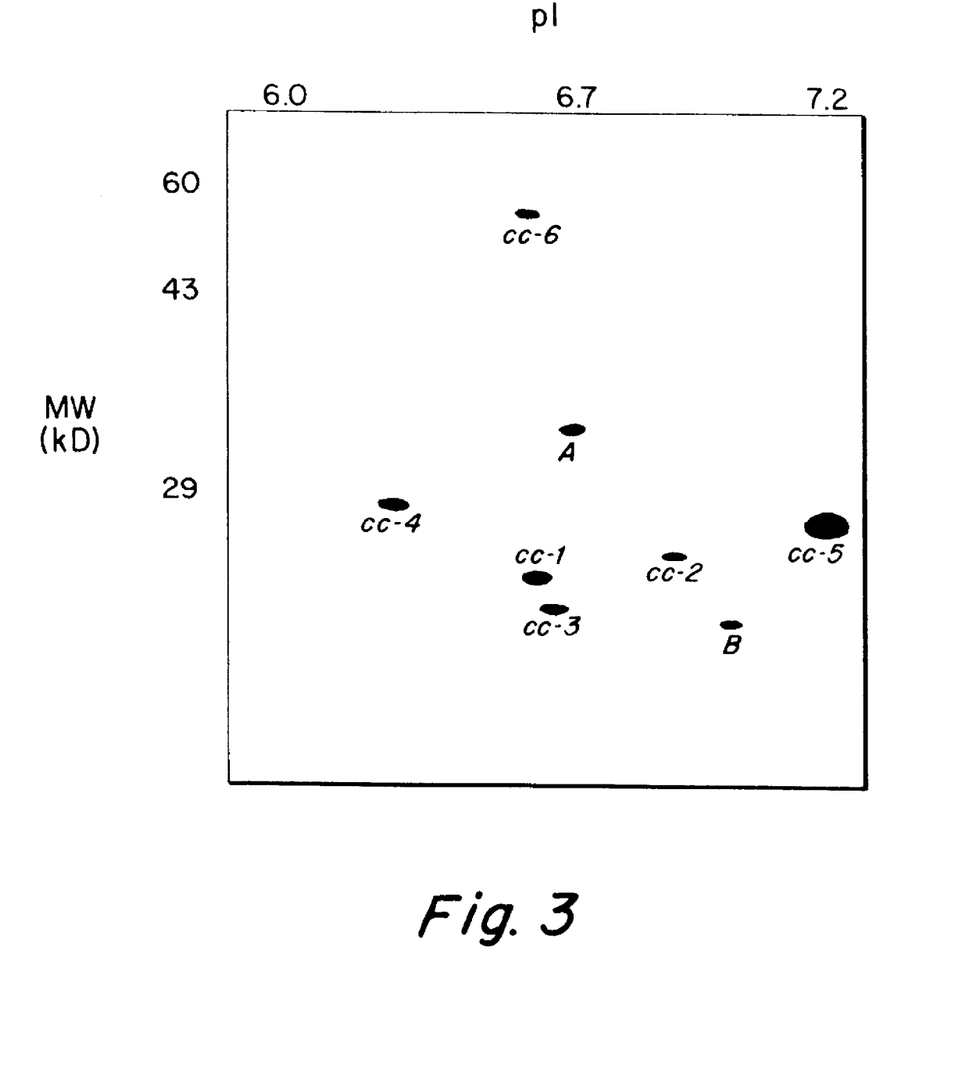
FIG. 3 is an illustration of a MasterScan image analysis of the colon-adenocarcinoma proteins shown in FIG. 1.
Figure 4:
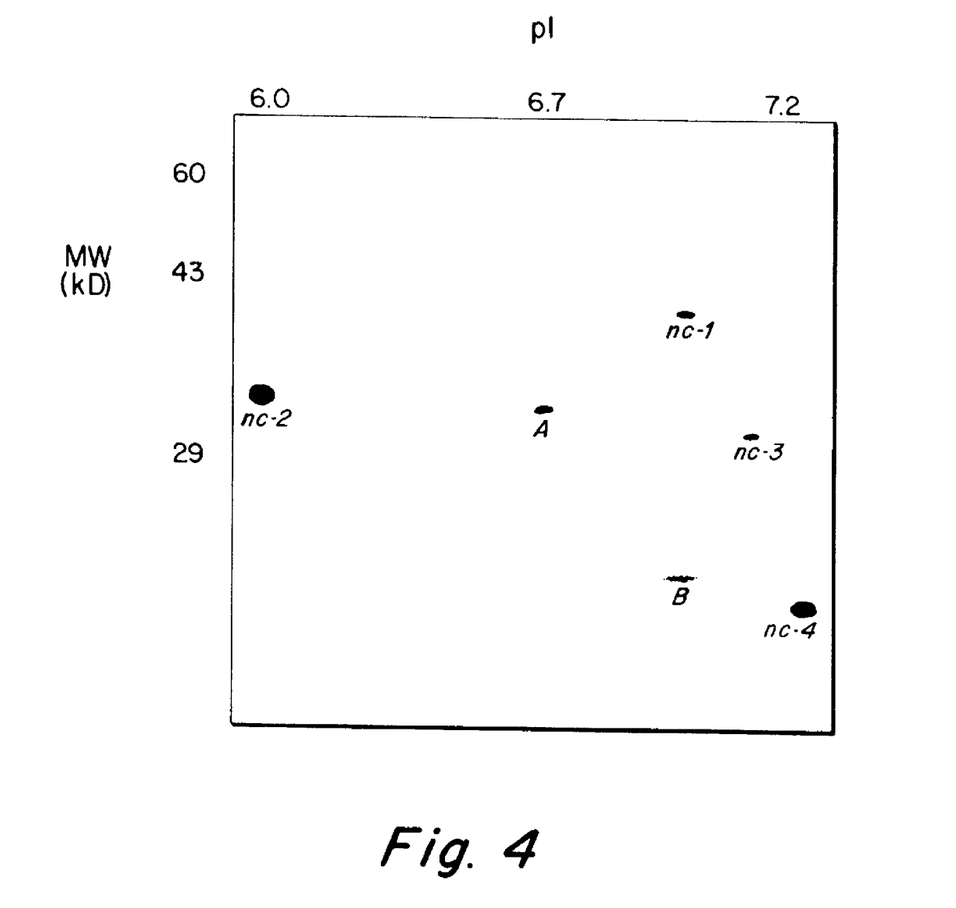
FIG. 4 is an illustration of a MasterScan image analysis of the proteins associated with normal colon tissue shown in FIG. 2.

MasterScan Image analysis of the gels in FIGS. 1 and 2 also was conducted, as described in Section III.E. FIG. 3 is an illustration of a MasterScan image analysis of the proteins isolated from colon cancer (CC) tissue shown in FIG. 1. FIG. 4 is an illustration of a MasterScan image analysis of the proteins isolated from normal colon tissue (NC) shown in FIG. 2. Proteins marked A and B in FIGS. 3 and 4 represent proteins common to both tumor and normal tissues. In FIGS. 1–4, molecular weight (MW) in thousands is plotted versus isoelectric point (pI) in pH units.

The MasterScan images in FIGS. 3 and 4 highlight the tumor and normal colon cell-associated proteins, and also show two invariant proteins present in both normal and tumor tissues. The molecular weight for each protein was computed by triangulation from known standards (see Tables 1, 2). The values of molecular weight in the tables are approximate, and are accurate to within approximately ±1,000. An overlay program which directly compares two gel electropherograms by matching common proteins did not detect any overlap between colon tumor cell-associated and normal colon cell-associated proteins thus confirming the tumor association of the proteins identified by visual observation.

It is thus observed that the colon adenocarcinoma-associated proteins are found within all colon adenocarcinoma samples utilized despite variations in detailed tumor properties. Without being limited to any theory, the colon adenocarcinoma-associated proteins isolated as described herein (essentially by the method of Penman and Fey, described in U.S. Pat. Nos. 4,882,268 and 4,885,236) appear to originate from the nuclear matrix of the colon adenocarcinoma cell. The nuclear matrix appears to be fundamentally involved in transcriptional control, which presumably includes alteration in the normal cellular phenotype as a consequence of tumor development. Fey et al., *Crit. Rev. Euk. Gene Express*, 1:127–143 (1991)). Accordingly, the isolated proteins described herein may be directly involved in altered gene regulation, and may therefore provide unambiguous markers for colon adenocarcinomas as well as targets for cancer therapy.

G. Identification of Colon Tumor-Associated Proteins from Cell Lines

The colon tumor-associated proteins also were isolated from tumor cell lines derived from colon adenocarcinomas, as described in Section III.B-C. The colon tumor cell lines all were derived from epithelial adenocarcinoma. In a separate analysis, non-target protein containing fractions, obtained during isolation of the target proteins from the cell line DLD, also were analyzed. AS illustrated in Table 4, the target

TABLE 4

| Cellular Fraction | Target Proteins Expressed | | | | | |
|---|---|---|---|---|---|---|
| | CC-1 | CC-2 | CC-3 | CC-4 | CC-5 | CC-6 |
| Soluble | – | – | – | – | – | – |
| Soluble Cytoskeletal | – | – | – | – | – | – |
| Chromatin | – | – | – | – | – | – |
| Target Protein | + | + | + | + | + | + |

TABLE 5

| Tumor Cell Line | Tumor of Orgin Dukes Stage* | Target Proteins Expressed | | | | | |
|---|---|---|---|---|---|---|---|
| | | CC-1 | CC-2 | CC-3 | CC-4 | C-5 | CC-6 |
| DLD | C | – | +/– | + | +++ | + | + |
| HT-29 | NA** | + | +/– | + | + | +/– | + |
| LoVo*** | NA | – | – | +/– | ++ | – | – |

TABLE 5-continued

| Tumor Cell Line | Tumor of Orgin Dukes Stage* | Target Proteins Expressed | | | | | |
|---|---|---|---|---|---|---|---|
| | | CC-1 | CC-2 | CC-3 | CC-4 | C-5 | CC-6 |
| COLO*** | D | − | + | + | + | + | − |
| Caco*** | NA | + | + | + | + | + | + |
| SW-1116 | A | + | − | − | + | + | + |

*1932 Dukes Classification
**NA, not available
***Tumor cell lines arising from metastatic adenocarcinoma originating from colon proteins were not found in any of the other fractions isolated from the colon tumor cell line DLD. Additionally, as illustrated in Table 5, each of the colon adenocarcinoma-associated proteins isolated from colon tissue, CC-1 through CC-6, can be detected in one or more colon tumor cell lines, supporting the epithelial cell origin of each protein.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for detecting the presence of an adenocarcinoma of the colon in a mammal comprising:
   detecting the presence of a colon adenocarcinoma-associated protein in a tissue or body fluid sample of a mammal, wherein the colon adenocarcinoma-associated protein is selected from the group consisting of
      a protein having a molecular weight of about 22,359 and an isoelectric point of about 6.6;
      a protein having a molecular weight of about 23,505 and an isoelectric point of about 6.9;
      a protein having a molecular weight of about 20,838 and an isoelectric point of about 6.7; and
      a protein having a molecular weight of about 58,600 and an isoelectric point of about 6.6;
   wherein the isoelectric point is determined by standard isoelectric focusing techniques, and the molecular weight is determined by standard polyacrylamide gel electrophoresis techniques, and wherein said protein is further characterized as being a non-cytoskeletal, non-chromatin protein that is detectable on a silver stained gel produced by two dimensional gel electrophoresis of proteins isolated from mammalian colon adenocarcinoma cells but is not detectable on a silver stained gel produced by two dimensional gel electrophoresis of proteins isolated from normal mammalian colon cells;
   thereby to indicate the presence of an adenocarcinoma of the colon in the mammal.

2. The method of claim 1 wherein a plurality of the colon adenocarcinoma-associated proteins are detected, thereby to indicate the presence of an adenocarcinoma of the colon in the mammal.

3. The method of claim 2 wherein said method further comprises, prior to said detecting step, the step of isolating the colon adenocarcinoma-associated proteins from the sample; and
   wherein said detecting step comprises:
      separating the proteins by two dimensional gel electrophoresis, thereby to produce a two dimensional gel electrophoresis pattern; and
      comparing the gel electrophoresis pattern with a standard.

4. The method of claim 3 wherein the standard is obtained from a data base of electrophoresis patterns.

5. The method of claim 1 or 3 wherein the colon adenocarcinoma-associated protein is a nuclear matrix protein.

6. The method of claim 1 wherein the colon adenocarcinoma-associated protein is detected in a colon tissue sample.

7. The method of claim 1 wherein the colon adenocarcinoma-associated protein is detected in a body fluid sample selected from the group consisting of a blood, serum, plasma, fecal, urine, semen, vaginal secretion, spinal fluid, saliva, ascitic fluid, peritoneal fluid, sputum, and a body exudate sample.

8. The method of claim 1 wherein the colon adenocarcinoma-associated protein is associated with a metastasized adenocarcinoma of the colon; and
   wherein the presence of the protein is detected, thereby to indicate the presence of a metastasized adenocarcinoma of the colon in the mammal.

9. The method of claim 1 further comprising detecting in the tissue or body fluid sample of the mammal the absence of a protein associated with normal colon cells, and not associated with colon adenocarcinoma cells, thereby to indicate the presence of the colon adenocarcinoma in the mammal.

10. The method of claim 9 wherein the protein associated with normal colon cells, and not associated with colon adenocarcinoma cells, is selected from the group consisting of
   a protein having a molecular weight of about 40,640 and an isoelectric point of about 7.0;
   a protein having a molecular weight of about 32,240 and an isoelectric point of about 6.0;
   a protein having a molecular weight of about 30,939 and an isoelectric point of about 7.2; and
   a protein having a molecular weight of about 17,400 and an isoelectric point of about 7.3;
   wherein the isoelectric point is determined by standard isoelectric focusing techniques, and the molecular weight is determined by standard polyacrylamide gel electrophoresis techniques.

11. The method of claim 9 wherein the protein associated with normal colon cells and the protein associated with colon adenocarcinoma cells are each nuclear matrix proteins.

12. The method of claim 1 wherein said method comprises:
   reacting the sample with a labeled binding moiety capable of specifically binding the colon adenocarcinoma-associated protein, to form a labeled complex of the binding moiety and the colon adenocarcinoma associated protein; and
   detecting the labeled complex, thereby to indicate the presence of an adenocarcinoma of the colon in the mammal.

13. The method of claim 12 wherein the labeled binding moiety comprises a labeled antibody.

14. The method of claim 13 wherein said labeled antibody is an isolated antibody to an isolated colon adenocarcinoma-associated protein wherein said protein is further characterized as being detectable by two dimensional gel electrophoresis of proteins isolated from colon adenocarcinoma cells, and not detectable by two dimensional gel electrophoresis of proteins isolated from normal colon cells.

15. The method of claim 13 wherein said labeled antibody is an isolated antibody to an isolated, substantially pure colon adenocarcinoma-associated protein selected from the group consisting of:

a protein having a molecular weight of about 22,359 and an isoelectric point of about 6.6;

a protein having a molecular weight of about 23,505 and an isoelectric point of about 6.9;

a protein having a molecular weight of about 20,838 and an isoelectric point of about 6.7; and a protein having a molecular weight of about 58,600 and an isoelectric point of about 6.6;

wherein the isoelectric point is determined by standard isoelectric focusing techniques, and the molecular weight is determined by standard polyacrylamide gel electrophoresis techniques; and wherein said protein is further characterized as being detectable by two dimensional gel electrophoresis of proteins isolated from colon adenocarcinoma cells, and not detectable by two dimensional gel electrophoresis of proteins isolated from normal colon cells.

16. An isolated antibody to an isolated, substantially pure colon adenocarcinoma-associated protein selected from the group consisting of:

a protein having a molecular weight of about 22,359 and an isoelectric point of about 6.6;

a protein having a molecular weight of about 23,505 and an isoelectric point of about 6.9;

a protein having a molecular weight of about 20,838 and an isoelectric point of about 6.7; and a protein having a molecular weight of about 58,600 and an isoelectric point of about 6.6;

wherein the isoelectric point is determined by standard isoelectric focusing techniques, and the molecular weight is determined by standard polyacrylamide gel electrophoresis techniques, and wherein said protein is further characterized as being a non-cytoskeletal, non-chromatin protein that is detectable on a silver stained gel produced by two dimensional gel electrophoresis of proteins isolated from mammalian colon adenocarcinoma cells but is not detectable on a silver stained gel produced by two dimensional gel electrophoresis of proteins isolated from normal mammalian colon cells.

17. The isolated antibody of claim 16 to a colon adenocarcinoma-associated protein, said adenocarcinoma-associated protein being isolable from a mammalian cell sample by the steps of:

(a) extracting mammalian colon adenocarcinoma cells with an extracting solution comprising protease inhibitors, RNase inhibitors, and a non-ionic detergent-salt solution at physiological pH and ionic strength, to extract proteins in the nucleus and cytoskeleton which are soluble in the extracting solution;

(b) separating target colon adenocarcinoma-associated proteins from the cytoskeleton remaining in the extracted cells of step (a) by solubilizing the cytoskeleton proteins in a solution comprising protease inhibitors which does not dissolve the target proteins;

(c) separating the chromatin from the target proteins by digesting the insoluble material from step (b) with DNase in a buffered solution containing protease inhibitors; and (d) dissolving the insoluble target proteins from step (c) in a solubilizing agent comprising protease inhibitors, and dialyzing the dissolved target proteins into a physiological buffer comprising protease inhibitors, wherein the target proteins are soluble in the physiological buffer, and removing insoluble proteins from the solution.

* * * * *